United States Patent

Godin

[11] Patent Number: 5,314,473
[45] Date of Patent: May 24, 1994

[54] PROSTHESIS FOR PREVENTING GASTRIC REFLUX INTO THE ESOPHAGUS

[76] Inventor: Norman J. Godin, 14, Quai du Seujet, 1201 Geneva, Switzerland

[21] Appl. No.: 937

[22] Filed: Jan. 5, 1993

Related U.S. Application Data

[63] Continuation-in-part of Ser. No. 656,136, Mar. 11, 1991, abandoned.

[30] Foreign Application Priority Data

Jul. 20, 1989 [CH] Switzerland ............... 2703/89
Jul. 16, 1990 [WO] PCT Int'l Appl. ........... PCT/CH90/00171

[51] Int. Cl.⁵ .......... A61F 2/04; A61F 2/02; A61H 2/24
[52] U.S. Cl. ............... 623/12; 623/11; 623/2
[58] Field of Search ............... 623/2, 11, 12

[56] References Cited

U.S. PATENT DOCUMENTS

| | | |
|---|---|---|
| 15,192 | 6/1856 | Peale . |
| 3,898,701 | 8/1975 | La Russa . |
| 3,926,175 | 12/1975 | Allen . |
| 4,204,282 | 5/1980 | Bolt . |
| 4,218,782 | 8/1980 | Rygg . |
| 4,265,694 | 5/1981 | Boretos . |
| 4,403,604 | 9/1983 | Wilkinson . |
| 4,417,360 | 11/1983 | Moasser . |
| 4,451,936 | 6/1984 | Carpentier . |
| 4,605,407 | 8/1986 | Black . |
| 4,642,105 | 2/1987 | Toter . |
| 4,747,849 | 5/1988 | Galtier . |
| 4,759,758 | 7/1988 | Gabbay . |
| 4,763,653 | 8/1988 | Rockey . |
| 4,778,461 | 10/1988 | Pietsch . |
| 4,846,836 | 7/1989 | Reich . |
| 5,006,106 | 4/1991 | Angelchik . |
| 5,019,102 | 5/1991 | Hoene . |
| 5,084,061 | 1/1992 | Gau . |

FOREIGN PATENT DOCUMENTS

WO9101117 2/1991 PCT Int'l Appl. .

Primary Examiner—David Isabella
Assistant Examiner—Elizabeth M. Burke
Attorney, Agent, or Firm—Cushman, Darby & Cushman

[57] ABSTRACT

The prosthesis is configured like an anti-return valve ranged preferably in the area where the esophagus and the hiatal hernia meet. Said valve is comprised of a tubular part associated with an annular fixing element. The tubular part flattens progressively to form two joined lips. It is possible to form said valve with a wall thickness which increases from the free end of the lips towards the annular fixing part in order to avoid an easy returning under the effect of the surging pressure. During the passage of the alimentary bolus, the lips are spaced apart and joined again owing to their natural elasticity. A metal wire embedded in the annular fixing part is used for the radiologic marking.

11 Claims, 3 Drawing Sheets

PROSTHESIS FOR PREVENTING GASTRIC REFLUX INTO THE ESOPHAGUS

This application is a continuation-in-part of U.S. application Ser. No. 07/656,136, filed Mar. 11, 19931.

BACKGROUND OF THE INVENTION

1. Field of the Invention

The present invention relates to a prosthesis for preventing gastric reflux in the esophagus, including a valve associated with an annular fixation portion and having an opening that is elastically kept closed.

2. Description of the Related Art

Esophagitis is caused by chronic gastric reflux. Although the mucus of the stomach is capable of withstanding the highly acid pH of the gastric secretions, which is close to 1, this is not the case for the mucus of the esophagus. Consequently, when this reflux is chronic, it attacks the mucus of the esophagus and creates ulcers, which over the long term can cause shrinkage of the esophageal conduit.

This gastric reflux is generally associated with a hiatal hernia. The most currently used therapy for this type of affliction makes use of medicines. There are three categories: antacids, which tend to make the environment neutral by the intake of an alkaline product, $H_2$ antihistamines, which fix on the $H_2$ receptor of the parietal cell. Recently, a new medicine has been proposed that in turn blocks the production of $H^+$ ions by the parietal cell. However, this medicine has no further effect as soon as it ceases to be administered, and it cannot be taken continuously, because it might cause tumors, which has been confirmed at least for the rat. Finally, the third class comprises medicines that increase the motility of the esophagus and the stomach and tend to reduce the length of contact of the acid reflux with the esophagus. This therapy does not attack the primary cause of the ailment, which is gastric reflux, which reappears as soon as the treatment with medicine stops, so that the patient is forced to take medication permanently. This solution is clearly unsatisfactory both medically and economically.

As an alternative to this medication route, it has already been proposed to use an external prosthesis for mechanical opposition to gastric reflux. This external prosthesis is formed by an elastically extensible ring disposed around the end where the esophagus discharges into the stomach. By thus surrounding the base of the esophagus, the centripetal force that this ring exerts offers a flow resistance that tends to prevent gastric reflux from rising in the esophagus. Nevertheless, the effect of this ring is equally manifest with gastric reflux and with deglutition of the gastric contents. Consequently, the centripetal pressure cannot be selected to be too high, or else it may cause an unacceptable impairment to swallowing. The absence of selectivity in this solution in terms of the direction of flow does not make it possible to guarantee total efficacy of this external prosthesis. It has also been found that the external prosthesis can be pushed upward by the pressure of gastric reflux, so that the base of the esophagus is again exposed to attack by the acidity of the gastric juices. This ring is located outside the esophagus, and so its position cannot be further modified by endoscopy. Shifts of this external prosthesis in the abdominal cavity limit its use and can have risks.

These disadvantages explain why the use of this prosthesis is not widespread, because it does not offer a sufficient guarantee. If it fails, then recourse to medication must be made anew, and the proportion of failures has proved to be high. Finally, there are also surgical procedures, in particular the Nissen-Rossetti fundoplicature, which comprises making a sleeve with the gastric fundus surrounding the cardia, under the diaphragm. The disadvantage of such an operation is that in the case of deficient esophageal peristalsis it may cause severe dysphagia. Still other surgical procedures exist. Nevertheless, all the surgical solutions have postoperative risks, such as a recurrence of reflux after relaxation of the sutures, dysphagia when the sleeve is too tight, and sliding of part of the stomach upstream of the sleeve, thus causing severe reflux esophagitis. The patient thus operated upon can also neither burp nor vomit, which is difficult for some patients to tolerate.

A prosthesis of an elastomer material has also already been proposed in U.S. Pat. No. 4,846,836, and is intended to be placed in the esophagus and includes a cone inside a tubular portion intended for fixation of the prosthesis. The cone has a slit apex and is aimed toward the stomach, comprising a sort of funnel that ends in a valve, the slit of which is intended to open by the peristaltic thrust exerted on the gastric juicealimentary bolus, but to prevent flow in the opposite direction. A second slit, made between the base of the cone and the tubular portion, is intended to open under a certain reflux pressure to enable vomiting.

A major disadvantage of this prosthesis is due to the fact that the alimentary bolus must pass through a substantially reduced cross section of the valve at the apex of the cone; this cone is necessary to enable flow in reverse for access to the second opening intended for reflux in the case of vomiting. It is clear that such a valve comprises a certain hindrance to the patient, who will have difficulty in swallowing, particularly solids, because of the shrinkage at the passage through the slit, which can cause pain that is difficult to tolerate.

SUMMARY OF THE INVENTION

The object of the present invention is at least in part to overcome the disadvantages of the above arrangements.

To this end, the subject of this invention is a prosthesis for preventing gastric reflux in the esophagus, including a valve associated with an annular fixation part and having an opening the passage cross section of which is controlled by elastic means, characterized in that this valve is made from an element of generally tubular shape of an elastically deformable material, and a cross section of which is deformed progressively in a permanent manner in order to constrict the wall of this element at one of its ends, such that in the position of maximum spacing apart from the wall at this end, an opening substantially corresponding to the cross section of the tubular part located at the other end of this element is made, this constricted end being intended to be placed downstream of the tubular part of the element so that all the force applied against it, engendered by the peristaltic wave of the esophagus, tends to space these walls apart, while any force in the opposite direction tends to join them together, as long as it does not exceed a limit substantially greater than that generated by the peristaltic wave of the esophagus and thus causing the at least partial inversion of the tubular element.

The essential advantage of the proposed arrangement is due to the fact that the same valve, while it has a unidirectional effect, enables reflux when the pressure is sufficient, that is, in the case of vomiting. This valve also has the enormous advantage that in the open position it offers a passage cross section that is substantially equal to that of the esophagus, thus permitting easy swallowing of food.

BRIEF DESCRIPTION OF THE DRAWINGS

The accompanying drawing schematically and by way of example illustrates an embodiment and two variants of the prosthesis that is the subject of the present invention.

DETAILED DESCRIPTION OF THE PRESENTLY PREFERRED EXEMPLARY EMBODIMENTS

Figure 1:
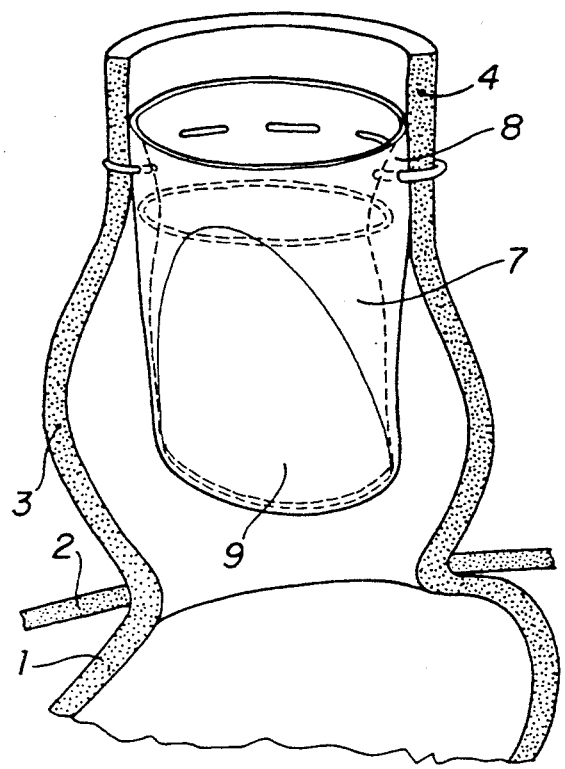
FIG. 1 is a perspective view in section of one embodiment of this prosthesis, affixed to the base of the esophagus.

FIG. 1 shows the top of the stomach 1, which has a hiatal hernia 3 of the diaphragm 2. Although gastric reflux is not always linked with the presence of such a hernia, nevertheless it is the most frequent cause of this affliction. The base of the esophagus 4 opens into this hiatal hernia 3.

Figure 2:
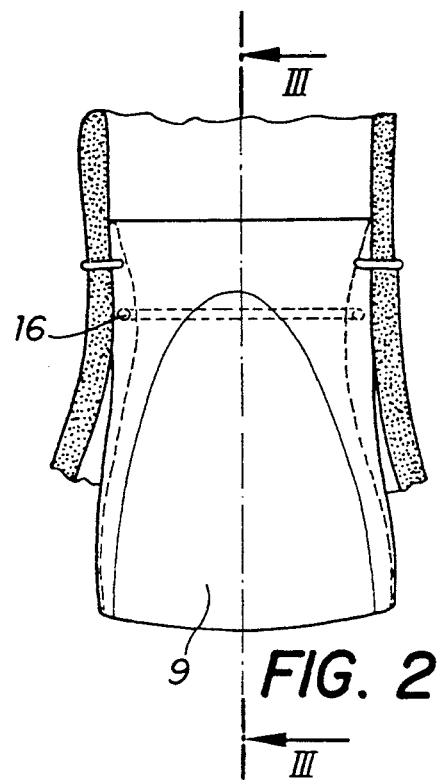
FIG. 2 is an elevational view of the embodiment of FIG. 1.
Figure 3:
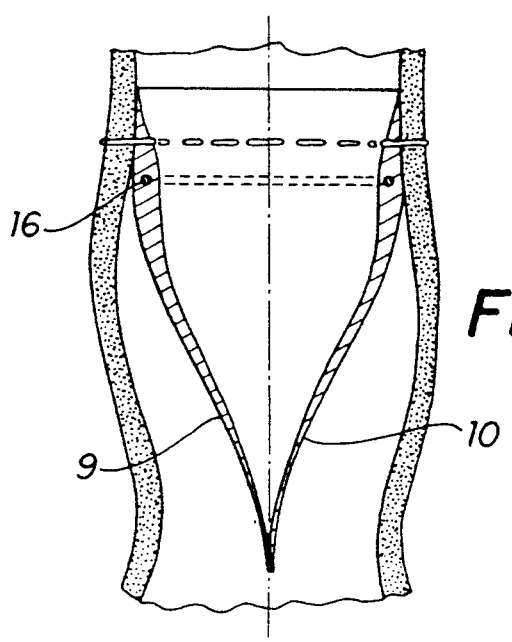
FIG. 3 is a sectional view along the line III—III of FIG. 2.

The embodiment shown in FIGS. 1-3 has a valve formed of a tubular portion 7 associated with an annular fixation element 8. This tubular portion, which moreover may itself form the fixation element, then flattens progressively to form two joined lips 9 and 10. This solution offers very slight resistance to the passage of the alimentary bolus and requires little or no capacity for extension, in so far as it suffices that the lips 9 and 10 are spaced apart from one another to allow passage to the flow. This prosthesis can be made from a silicone-based elastomer with two components of medical quality, sold under the mark Silastsic ® by Dow Corning Corporation, or it may be made of a biocompatible polymer such as that described in U.S. Pat. No. 4,657,544 or in U.S. Pat. No. 4,759,757, which can be suitable for such an application.

This is a solvent-free graft polymer with two hydrophilic or hydrophobic components, into which an inorganic water-soluble salt that has been ground and sifted is incorporated. A tube is then formed, and the salt crystals are washed out of the tube thus formed to make a honeycombed structure that increases flexibility and makes it possible to improve the adhesive bonding properties, in the case where this mode of fixation is used. Aside from the aforementioned elastomers, fluoroelastomer compounds such as Viton ® can be cited, along with rubbers of the butyl type. The valves can be formed with a wall thickness that increases from the free end of the lips 9 and 10 toward the annular fixation part 8, to avoid overly easy inversion under the influence of the reflux pressure. It can be noted that this embodiment affords a large surface area on which the reflux pressure can act to close the lips 9 and 10. If the tubular portion is slightly more rigid because of its increased thickness, the valve functions essentially by moving the lips 9 and 10 farther apart and closing them again.

As can also be observed in FIGS. 1-3, a very fine metal wire 16 can be embedded in the annular fixation element, with a view to permitting radiologic marking of the position of the valve.

Figure 4:
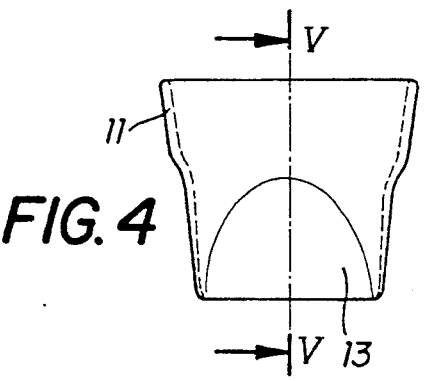
FIG. 4 is an elevational view of a variant of FIGS. 1-3.
Figure 5:
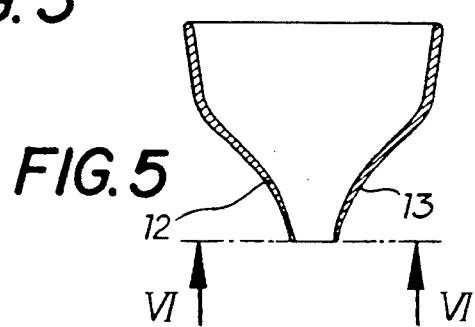
FIG. 5 is a sectional view along the line V—V of FIG. 4.

Other embodiments based on this same concept are conceivable. The variant shown in FIGS. 4 and 5 is distinguished essentially by the fact that the flattening of the annular portion 11 to form the lips 12 and 13 is much more sudden, thus reducing the axial dimension of the valve. This dimensional reduction has the advantage of occupying less space and making it possible to accommodate the prosthesis in its entirety in practically all hiatal hernias. In this example, the axial dimension of the prosthesis is on the order to 15 to 20 mm. However, the primary difference in this variant is the fact that in the position of repose, the two lips 12 and 13 remain separated as shown in FIG. 5, so as to facilitate the passage of the alimentary bolus and prevent food residues and saliva from remaining in the valve. By keeping the lips 12 and 13 apart, this risk is practically avoided, and saliva can flow into the stomach without the aid of any force for spacing the lips 12 and 13 apart. In this variant, the thickness of the wall of the level of the end of the lips 12 and 13 is on the order of 0.2 to 0.4 mm, while it thickens to attain a value of 1.2 to 1.7 mm in the annular portion 11.

In the case of gastric acid reflux, the pressure exerted on the outer faces of the flattened portions that form the lips 12 and 13 cause the closure of these lips. Even if a small quantity of gastric acid passes between the lips, this reflux does not threaten to exceed the level of the valve and hence to attack the esophageal mucus. As soon as the reflux pressure disappears, the lips 12 and 13 move apart again to the position of repose shown in FIG. 5 and allow the acid that may be located in the valve to drop downward again.

If the reflux pressure increases substantially, which occurs only in the case of vomiting, the lips 12 and 13 invert and allow the flow to pass in the opposite direction. In the variant shown in FIGS. 4 and 5, it has been found that in the case of inversion, these lips return to their initial position by their intrinsic elasticity.

Figure 6:
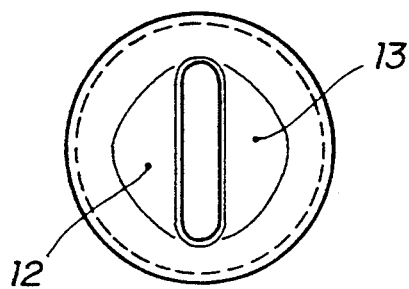
FIG. 6 is a sectional view along the line VI—VI of FIG. 5.
Figure 7:
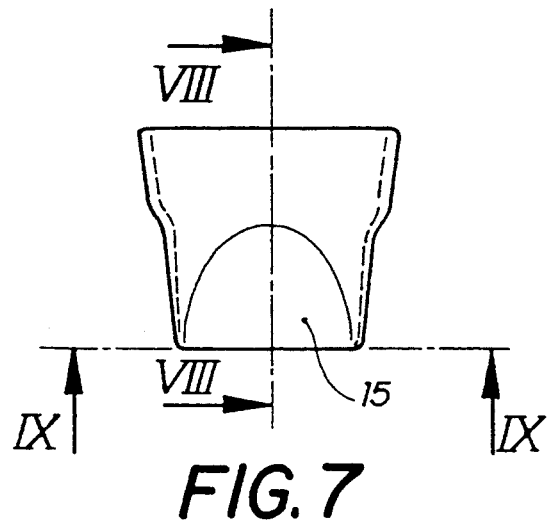
FIG. 7 is a view similar to FIG. 4, of a variant.
Figure 8:
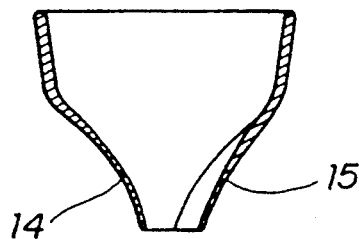
FIG. 8 is a sectional view along the line VIII—VIII of FIG. 7.
Figure 10:
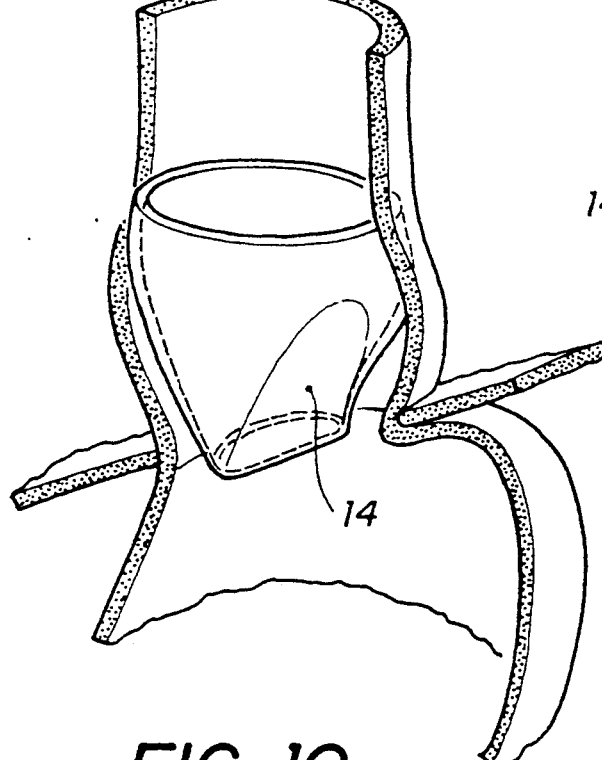
FIG. 10 is a perspective view of the variant of FIGS. 7-9, disposed in a hiatal hernia.
Figure 9:
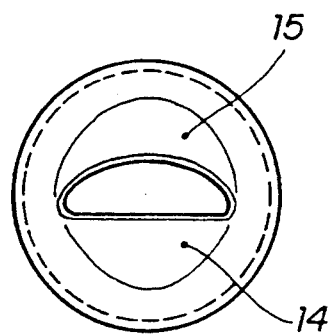
FIG. 9 is a view along the line IX—IX of FIG. 7.

The second variant shown in FIGS. 7-10 differs from that of FIGS. 4 and 5 in that the lips 14 and 15 are asymmetrical, forming a D-shaped opening between them instead of the elongated 0 formed by the opening between the symmetrical lips 12 and 13. The reason for the choice of this asymmetrical form of the opening made between the lips 14 and 15 is the fact that the stomach itself has an asymmetrical shape, as illustrated in FIG. 6, such that the reflux pressure that is exerted on the lips 14 and 15 is not vertical but rather lateral, and that the lip 14 is thus subjected to higher pressure than the lip 15. Providing the lip 15 with a convex shape thus further facilitates the passage of the gastric juices. Contrarily, the straight lip 14 offers less resistance to deformation, and since it is subjected to the greatest reflux pressure, which comes from the right, it is pressed against the lip 15 and closes the orifice of the passage in case of reflux, with the lip 15 remaining practically immobile.

Figure 11:
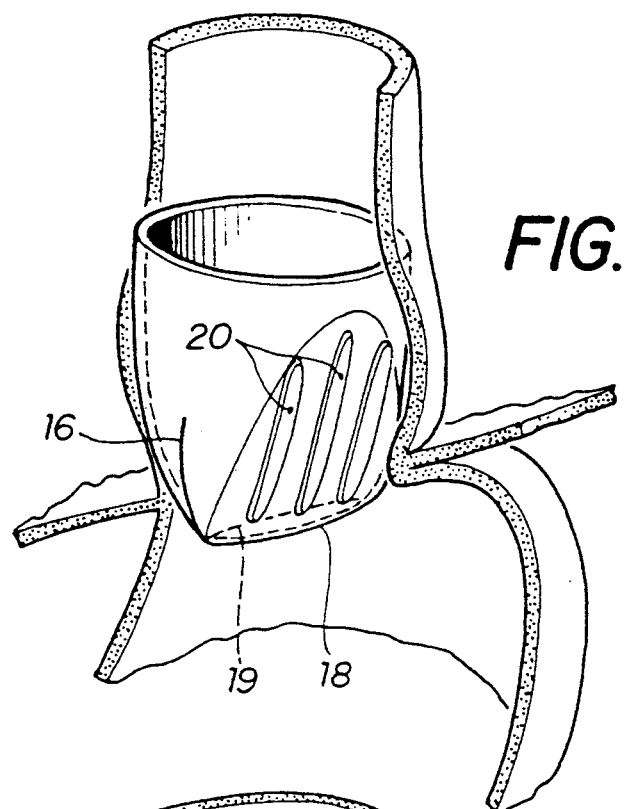
FIG. 11 is a perspective view of a further variant disposed in a hiatal hernia.
Figure 12:
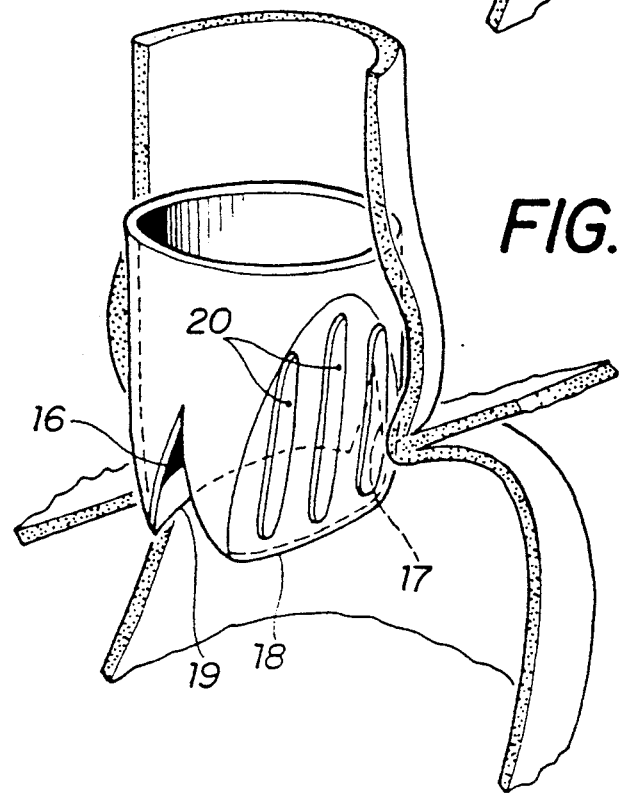
FIG. 12 is a perspective view of the variant of FIG. 11 with the lips separated for the passage of an alimentary bolus.

The third variant shown in FIGS. 11 and 12 is distinguished essentially by the fact that two diametrically opposed slits 16, 17 are provided which separate the lips 18 and 19 of the valve from each other so that, when the alimentary bolus is driven toward the stomach by the peristaltic wave of the esophagus, the edges of each lip 18 and 19 move apart. The slits 16, 17 make the opening of the valve easier so that the lips 17, 18 may be slightly stiffened by ribs 20. Such ribs increase resistance to reflux pressure and promote the recovery of initial form of the valve when the pressure of reflux, in the case of vomiting, is sufficient to turn up the lips 17, 18.

I claim:

1. A prosthesis for preventing gastric reflux into an esophagus comprising:

a valve means for controlling a flow direction through the esophagus, said valve means having first and second ends, a longitudinal axis, a generally tubular, resilient side wall, and a flow passage defined therethrough, said valve means being formed from a resilient, bicompatible material and being implantable;

said first end of said valve means having a circular cross-section substantially corresponding to a cross-section of the esophagus to allow fixation of said first end to a wall of a hiatal hernia of the esophagus;

the resilient side wall of said valve means being progressively, resiliently collapsed adjacent said second end thereby defining a segment of said valve means having resiliently collapsed side walls to at least substantially constrict said flow passage at said second end of said valve means, so that when said valve means is secured to the wall of the hiatal hernia with said second end disposed downstream of the first end, 1) any force generated on an alimentary bolus by a peristaltic wave of the esophagus tends to space apart the resiliently collapsed side walls whereby the second end of said valve means can offer a passage cross-section that is substantially equal to that of the first end of the valve means, 2) a regurgitate gastric reflux force which is substantially greater than a force of a peristaltic wave urges said resiliently collapsed side walls to invert to a position of repose to define, solely for a duration of said gastric reflux force, a flow path for vomit, and 3) any gastric reflux force which is not substantially greater than a force of a peristaltic wave urges said resiliently collapsed side walls to substantially close side walls to substantially close said second end, thereby to substantially prevent gastric reflux into the esophagus.

2. A prosthesis as claimed in claim 1, wherein said second end of said valve means defines an opening having a cross-section less than a cross-section of the first end when the valve means is in said position of repose.

3. A prosthesis as claimed in claim 1, wherein said tubular side wall of said valve means progressively thins along a portion of a length thereof.

4. A prosthesis as claimed in claim 1, further comprising first and second longitudinal, diametrically opposed slits in said tubular side wall which extend from said second end along a portion of a length of the valve means, thereby to facilitate opening of said second end for passage of an alimentary bolus.

5. A prosthesis as claimed in claim 4, further comprising at least one reinforcing rib provided on said side wall adjacent said second end to stiffen said side wall adjacent said second end.

6. A prosthesis as claimed in claim 5, wherein said at least one reinforcing rib extends longitudinally of said side wall.

7. A prosthesis as claimed in claim 5, wherein said reinforcing rib is defined on an exterior surface of said side wall and integrally molded with said valve means.

8. A prosthesis as claimed in claim 1, further comprising at least one reinforcing rib provided on said side wall adjacent said second end to stiffen said side wall adjacent said second end.

9. A prosthesis as claimed in claim 8, wherein said reinforcing rib extends longitudinally of said side wall.

10. A prosthesis as claimed in claim 8, wherein said reinforcing rib is defined on an exterior surface of said side wall and integrally molded with said valve means.

11. A prosthesis as claimed in claim 1, wherein said resiliently collapsed side walls as collapsed symmetrically with respect to a plane comprising the longitudinal axis of said valve means.

* * * * *